US010323786B2

(12) United States Patent
Hörndler et al.

(10) Patent No.: US 10,323,786 B2
(45) Date of Patent: Jun. 18, 2019

(54) MANUALLY ADJUSTABLE MONITOR BRACKET FOR A FLAT PANEL DISPLAY OF A MOBILE DIAGNOSTIC DEVICE

(71) Applicant: Ziehm Imaging GmbH, Nürnberg (DE)

(72) Inventors: Klaus Hörndler, Nürnberg (DE); Ewald Hauser, Nürnberg (DE)

(73) Assignee: Ziehm Imaging GmbH, Nürnberg (DE)

( * ) Notice: Subject to any disclaimer, the term of this patent is extended or adjusted under 35 U.S.C. 154(b) by 165 days.

(21) Appl. No.: 15/141,454

(22) Filed: Apr. 28, 2016

(65) Prior Publication Data

US 2016/0319986 A1 Nov. 3, 2016

(30) Foreign Application Priority Data

Apr. 30, 2015 (DE) .................. 10 2015 005 505

(51) Int. Cl.
*F16M 11/10* (2006.01)
*F16M 11/20* (2006.01)
(Continued)

(52) U.S. Cl.
CPC ....... *F16M 11/2064* (2013.01); *A61B 5/7445* (2013.01); *A61B 8/4405* (2013.01);
(Continued)

(58) Field of Classification Search
CPC ..... A61B 5/7445; A61B 8/4405; A61B 8/462; F16M 11/12; F16M 11/2007;
(Continued)

(56) References Cited

U.S. PATENT DOCUMENTS 4,770,384 A * 9/1988 Kuwazima ............. F16M 11/10
248/280.11
5,108,061 A * 4/1992 Vlasak ............... F16M 11/2021
248/162.1
(Continued)

FOREIGN PATENT DOCUMENTS

DE 40 14 009 10/1991
DE 20 2005 009 471 11/2005
(Continued)

*Primary Examiner* — Jonathan Liu
*Assistant Examiner* — Guang H Guan
(74) *Attorney, Agent, or Firm* — Knobbe Martens Olson & Bear LLP

(57) ABSTRACT

The present disclosure relates to a manually adjustable monitor bracket for a flat panel display of a mobile diagnostic device that includes at least two joints with mutually parallel pivot axes, the joints being connected to one another by a first arm. In order to prevent a collision of the flat panel screen attached to a hand joint on a second arm and/or of the monitor bracket with an obstacle whose position relative to the coordinate system of the mobile diagnostic device is known, in particular with a part of the diagnostic device, the monitor bracket includes a device for preventing a collision that limits the movement of the monitor bracket in such a manner that movement in a direction about the first horizontal pivot axis or in a direction about the second horizontal pivot axis is blocked if a continuation of the movement about the pivot axes would lead to the value pairs consisting of the pivot angles of the shoulder joint and of the pivot angles of the elbow joint being contained in the number of the value pairs of the pivot angles of the collision-endangered area.

5 Claims, 3 Drawing Sheets

(51) Int. Cl.
*A61B 5/00* (2006.01)
*A61B 8/00* (2006.01)
*F16M 11/18* (2006.01)
*F16M 11/42* (2006.01)
*F16M 11/24* (2006.01)

(52) U.S. Cl.
CPC ............ *A61B 8/462* (2013.01); *F16M 11/10* (2013.01); *F16M 11/18* (2013.01); *F16M 11/2021* (2013.01); *F16M 11/2092* (2013.01); *F16M 11/24* (2013.01); *F16M 11/42* (2013.01); *F16M 2200/022* (2013.01); *F16M 2200/044* (2013.01); *F16M 2200/063* (2013.01)

(58) Field of Classification Search
CPC ........... F16M 11/2021; F16M 11/2035; F16M 11/2057; F16M 11/2064; F16M 11/2071; F16M 13/02; F16M 2200/02; F16M 2200/021; F16M 2200/022; F16M 2200/044; F16M 2200/063
USPC ..... 248/276.1, 280.11, 284.1, 291.1, 292.13; 600/437
See application file for complete search history.

(56) References Cited

U.S. PATENT DOCUMENTS

| | | | | |
|---|---|---|---|---|
| 6,115,068 | A * | 9/2000 | Ariga | F16M 11/18 348/207.99 |
| 6,669,639 | B1 * | 12/2003 | Miller | A61B 8/00 600/443 |
| 7,626,569 | B2 * | 12/2009 | Lanier | G06F 1/1601 345/156 |
| 7,775,485 | B2 * | 8/2010 | Asai | A61B 8/14 248/125.7 |
| 8,496,218 | B2 * | 7/2013 | Ochoa | F16M 11/10 248/276.1 |
| 9,408,452 | B1 * | 8/2016 | Al-Khulaifi | A45D 20/12 |
| 2005/0062238 | A1 * | 3/2005 | Broadfield | A61G 12/001 280/1 |
| 2012/0230668 | A1 * | 9/2012 | Vogt | G03B 17/561 396/428 |
| 2014/0226281 | A1 * | 8/2014 | Emami | F16M 13/00 361/679.56 |
| 2015/0369418 | A1 * | 12/2015 | Wong | F16M 11/041 248/372.1 |
| 2016/0120507 | A1 * | 5/2016 | Ninomiya | A61B 8/4405 345/1.3 |
| 2016/0296297 | A1 * | 10/2016 | Perplies | A61G 12/004 |
| 2016/0319986 | A1 * | 11/2016 | Horndler | A61B 8/4405 |

FOREIGN PATENT DOCUMENTS

| | | |
|---|---|---|
| DE | 10 2007 059 312 | 7/2008 |
| EP | 1 880 678 | 1/2008 |
| KR | 10 2010 0 047 436 | 5/2010 |
| WO | WO 2005/074807 | 8/2005 |

* cited by examiner

MANUALLY ADJUSTABLE MONITOR BRACKET FOR A FLAT PANEL DISPLAY OF A MOBILE DIAGNOSTIC DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure relates to a manually adjustable monitor bracket for a flat panel display of a mobile diagnostic device.

Description of Related Art

From medical diagnostics, in particular from imaging X-ray or ultrasound diagnostics, mobile diagnostic devices are known that comprise a monitor, in particular a flat panel display to allow an operator to view images. It is known to arrange the monitor in a manner such that it can be adjusted on the mobile diagnostic device, in order to improve the ergonomics of monitor use.

Manually adjustable monitor brackets for mobile diagnostic devices are known from the patent literature.

From the PCT Application WO05074807A1 an ultrasound examination system with a multiply adjustable bracket for a flat panel display is known, wherein the bracket comprises a parallelogram guide system and the [sic] is compensated by the weight force of the flat panel display and of a support arm by means of a lever arrangement with a gas spring.

From the document U.S. Pat. No. 6,669,639B1, a monitor bracket with a support arm on a mobile ultrasound diagnostic device is known, wherein the bracket comprises three joints with mutually separated parallel vertical axes and at least one joint has an angular movement that can be limited in order to prevent a collision of the support arm with the diagnostic device.

From EP1880678B1, a manually adjustable monitor bracket with a cable guide integrated in the monitor bracket is known, wherein the monitor can be shifted about three parallel vertical axes.

From DE102007059312A1, a manually adjustable monitor bracket is known, which comprises a locking mechanism by means of which an unintentional collision movement of the monitor with a wall during the movement of the mobile unit is prevented.

From the document KR1020100047436A1, a monitor bracket on a mobile ultrasound diagnostic device is known, in which sensors are provided for the detection of a risk of collision between the monitor and a part of the diagnostic device.

From the document DE202005009471U1, a monitor bracket with three joints with spaced apart vertical pivot axes is known, in which stops are provided for the delimitation of the adjustment angle in the joints.

From the document DE4014009A1, a support arm apparatus carrier for surveillance monitors with a parallelogram support and with a connecting rod arranged between said parallelogram support and the head support for the monitor is known, by means of which the head support is pivoted with positive control about a horizontal axis as a function of the adjustment movement of the parallelogram support.

Manually adjustable monitor brackets are known that detect a risk of collision or comprise devices for limiting a movement in an axis.

SUMMARY

There is a need for manually adjustable monitor brackets that comprise devices and/or components for preventing collisions of parts of the monitor arm and/or of the flat panel display with parts of the mobile diagnostic device, wherein the parts can be adapted to individually designed diagnostic devices in a cost effective way.

The above-identified need is addressed at least in part by the features of a manually adjustable monitor bracket for a flat panel display of a mobile diagnostic device with a shoulder joint rotatably mounted on an installation surface about a vertical rotation axis, on which shoulder joint a first arm is mounted such that it can be pivoted about a first horizontal pivot axis by a pivot angle WS between a first pivot angle, which is associated with a first stop, and a second pivot angle, which is associated with a second stop, wherein, on the side of the first arm, which faces away from the shoulder joint, an elbow joint with a second horizontal pivot axis parallel to the first horizontal pivot axis and with a second arm is arranged, wherein, between the first arm and the second arm, a pivot axis WE of the elbow joint can be adjusted between a third pivot angle, which is associated with a third stop, and a fourth pivot axis, which is associated with a fourth stop, and wherein the second arm comprises a hand joint, which supports an adjustable flat panel display, and wherein the monitor bracket comprises a device for preventing a collision of the flat panel display with the surface of the mobile diagnostic device, wherein a collision-endangered area is determined by a number of value pairs of pivot angles WS of the shoulder joint and pivot angles WE of the elbow joint, characterized in that the device for preventing a collision limits the movement of the monitor bracket in such a manner that a movement in a direction about the first horizontal pivot axis or in a direction about the second horizontal pivot axis is blocked if continuing the movement about the first horizontal pivot axes and the second horizontal pivot axis would lead to the value pairs consisting of the pivot angles WS of the shoulder joint and of the pivot angles WE of the elbow joint that are contained in the number of value pairs of pivot angles of the collision-endangered area.

BRIEF DESCRIPTION OF THE DRAWINGS

The invention is explained in further detail in reference to the drawings.

DETAILED DESCRIPTION

Figure 1:
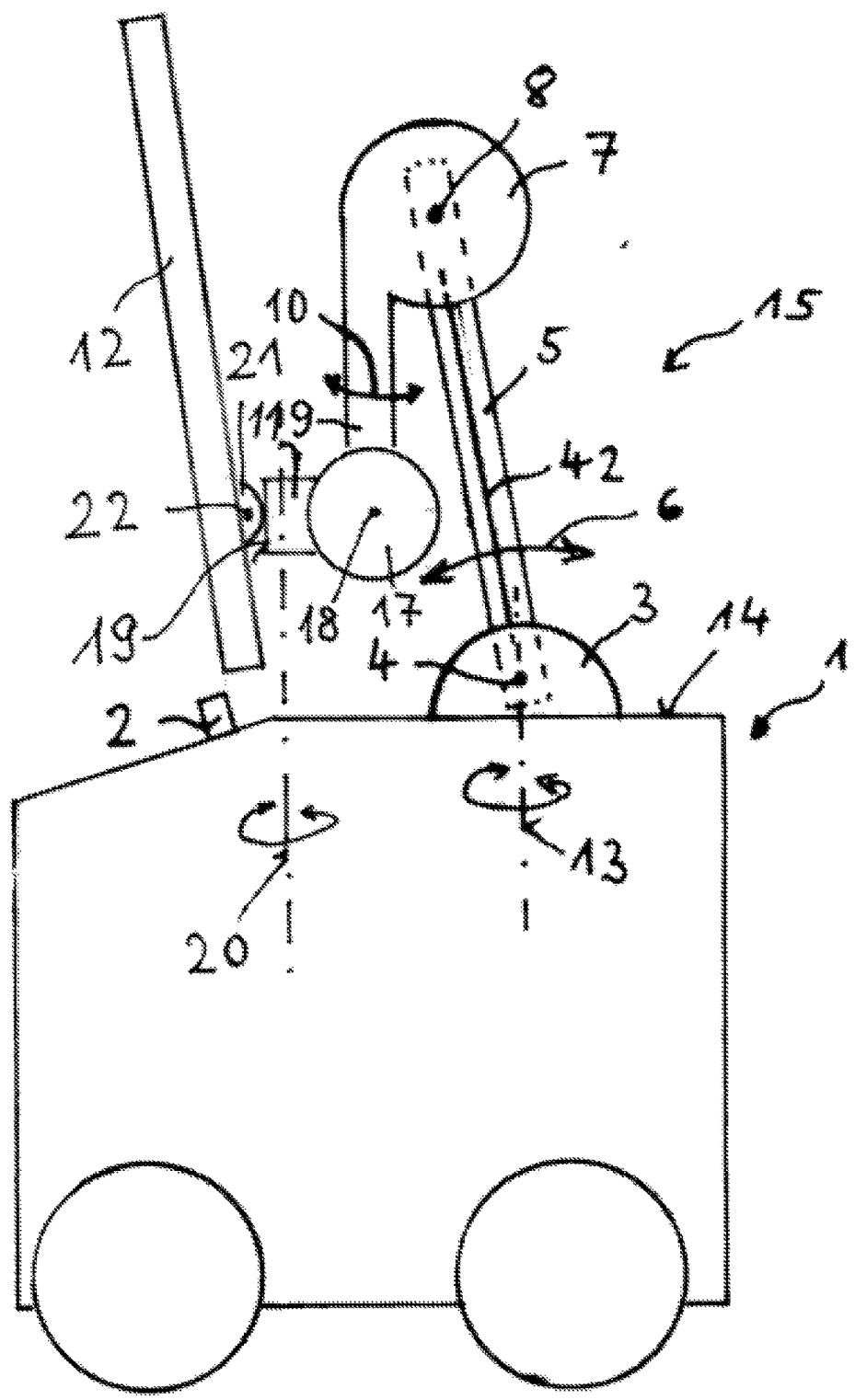
FIG. 1: Monitor bracket on, a mobile diagnostic device.

FIG. 1 represents a mobile diagnostic device 1 with, for example, an operating element 2 and an installation surface 14 for the monitor bracket 15. The operating element 2 is representative of the operating elements of the diagnostic device. Depending on the functionality desired by the user, the number and the arrangement of the operating elements 2 can vary within an operating field, which consequently would benefit from individually adaptable ways to prevent collisions. The monitor bracket 15 comprises a shoulder joint 3 arranged on the installation surface 14, which can be rotated about a vertical rotation axis 13 with respect to the installation surface 14. The shoulder joint 3 comprises a first horizontally arranged pivot axis 4 about which a first arm 5 can be pivoted in the pivot direction 6. At the end of the first arm 5, which faces away from the installation surface 14, a second horizontal pivot axis 8 is arranged, which supports an elbow joint 7 with a second arm 9 arranged thereon, which is pivotable in the movement direction 10 relative to the first arm 5.

In a parked position of the monitor bracket 15, which is set up in the procedure of the mobile diagnostic device 1, a lock is provided in all the joints. In particular, in the shoulder joint 3, it is provided to allow a locking brake to act simultaneously on the first horizontal pivot axis 4 and on the vertical rotation axis 13.

The second arm 9 supports a hand joint 17 which can be pivoted about a third horizontal pivot axis 18, with a hand 11 that supports a support plate 19 that is held in a manner such that it can be rotated with limitation about a vertical rotation axis 20. On the support plate 19, the flat panel display 12 is held by a pivot bearing 21 such that it can be pivoted with limitation about a fourth horizontal pivot axis 22.

The monitor bracket 15 comprises a double parallelogram connecting rod arrangement with three horizontal pivot axes 4, 8, 18, wherein weight compensation devices are arranged in, the arms 5 and 9.

The double parallelogram connecting rod arrangement with the arms 5 and 9 and with the three horizontal pivot axes 4, 8, 18 is designed in such a manner that the hand rotation axis 20 of the hand 11 remains vertical over the entire adjustment area of the monitor bracket 15 and thus is always oriented parallel to the vertical rotation axis 13.

The weight forces of the flat panel display 12 and of the arms 5, 9 as well as of the joints 7, 17 generate torques that act in the direction of the adjustment of the joints. The monitor bracket 15 can include components configured to generate, by tension or pressure screw springs or gas compression springs, corresponding counter torques and/or to stabilize the monitor bracket 15 by increasing the friction in the joints 3, 7 and 17. The components for torque compensation are not represented in the figures.

In addition to the coupling of the shoulder joint and the elbow joint 7 by way of the double parallelogram connecting rod arrangement, the shoulder joint 3 and the elbow joint 7 comprise an additional coupling. This additional coupling is represented diagrammatically in FIG. 1 by a rod-shaped control element 42. The coupling of the joints occurs in a manner such that certain combinations of a pivot angle of the first arm 5 in the shoulder joint 3 cannot be set and a pivot angle of the second arm 9 in the elbow joint 7 cannot be set by locking of the joints 3 and 7.

The additional coupling is not limited to a mechanical coupling. For example, in the context of the described embodiments, the angles of the joints can be determined by way of rotary encoders and locking of the joints can be accomplished by way of an electromotor or electromechanical devices.

In FIG. 1, a rod-shaped control element 42 is represented, which produces the opposite-side locking of the joints 3 and 7 by collaboration with cam disks in the joints 3, 7. As a result of the design of the cam disks and their orientation opposite one another, collisions of the flat panel display 12 with the mobile diagnostic device 1 and, in particular, with an operating element 2 of the mobile diagnostic device are prevented. The coupling mechanism including cam disks and control element 42 allows an operator to freely move the flat panel display 12 outside of the collision-endangered areas within the limits of the admissible adjustment areas of the monitor bracket 15.

The additional coupling limits the extent of movement of the one joint 3, 7 relative to the position of the adjacent other joint 7, 3 within the respective admissible adjustment area of the joints 3, 7.

Due to the limited pivoting movements in the axes 20 and 22, the flat panel display 12 can be adjusted manually relative to the support plate 19 in such a manner that an ergonomic viewing of the flat panel display 12 by an operator is made possible.

Figure 2:
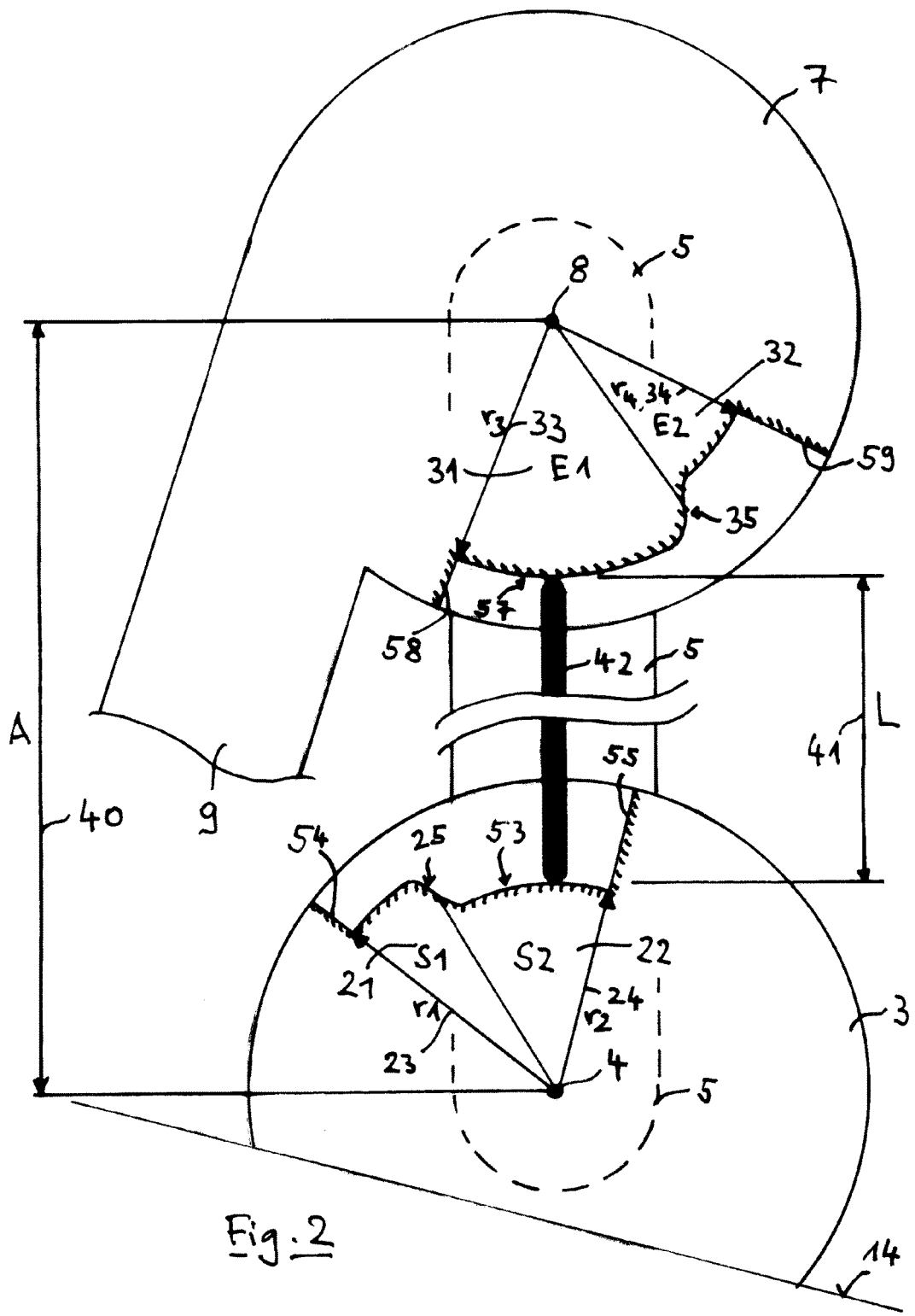
FIG. 2: Locking device for collision prevention with mutual influencing of adjacent joints.

In FIG. 2, the coupling mechanism is represented between the shoulder joint 3, arranged on the installation surface 14 of the mobile diagnostic device 1, and the elbow joint 7, connected by the first arm 5 to the shoulder joint 3, with the second arm 9 arranged on the elbow joint 7.

The first arm 5 can be pivoted in the shoulder joint 3 about a horizontal pivot axis 4 and in the elbow joint 7 about a second horizontal pivot axis 8. The joints 3, 7 comprise cam disks 53, 57, the curves of which are located in a plane perpendicular to the horizontal pivot axes 5, 8, which are arranged parallel to one another. In the plane of the cam disks 53, 57, a rod-shaped control element 42 on the connection line between the horizontal axes 4 and 8 is arranged on the first arm 5, and is held longitudinally slidably on the first arm 5.

The cam disk 53 of the shoulder joint 3 is limited by two stops 54, 55, which determine the admissible pivot range of the first arm 5 in the shoulder joint 3 in collaboration with the control element 42.

The cam disk 53 has a locking sector 21 and a release sector 22, each with curve sections in the shape of an arc of a circle, wherein the center of the circular arcs lies on the first horizontal pivot axis 4.

The locking sector 21 (S1) has a curve in the shape of an arc of a circle with a radius 23 (r1), the release sector 22 (S2) has a curve in the shape of an arc of a circle with a radius 24 (r2), wherein the radius 23 (r1) is greater than the radius 24 (r2). Between the circular arcs of the locking sector 21 and of the release sector 22, a transition area 25 is provided, by means of which the circular arcs with the different radii 23, 24 are consistently connected to one another.

The elbow joint 7 comprises a cam disk 57 which is delimited by two stops 58, 59 which, in collaboration with the control element 42, determine the admissible pivot range of the first arm 5 in the elbow joint 7 and thus the admissible pivot range of the second arm 9 relative to the first arm 5.

The cam disk 57 comprises a locking sector 31 and a release sector 32 with sections in the shape of an arc of a circle, wherein the center of the circular arcs lies on the second horizontal pivot axis 8. The locking sector 31 (E1) has a curve in the shape of an arc of a circle with a radius 33 (r3), the release sector 32 (E2) has a curve in the shape of an arc of a circle with a radius 34 (r4), wherein the radius 33 (r3) is greater than the radius 34 (r4). Between the circular arcs of the locking sector 31 and the release sector 32, a transition area 35 is provided such that the circular arcs with different radii 33, 34 are connected to one another.

The radii 23 (r1) and 33 (r3) can be selected to be of equal size; in the same way, the radii 24 (r2) and 34 (r4) can be selected to be of equal size.

The rod-shaped control element 42, which has a length 41, is guided along one of the two curves of the cam disks 53, 57 during the pivoting movements in the horizontal pivot axes 4 and 8. In some embodiments, the ends of the rod-shaped control element 42 can be in the shape of a sphere to reduce the sliding friction. In certain embodiments, mounted rollers can be provided at the ends of the rod-shaped control element 42, which roll on the cam disks 53, 54.

In order to achieve the locking action described herein, the rod-shaped control element 42 has a length 41 (L) which is in a relation with the separation 40 (A) of the horizontal axes 4, 8 and the radii 23, 24, 33, 34, (r1, r2, r3, r4) such that:

$$L = A - (r2 + r3 + x) \quad [1]$$

where x represents mechanical clearance to which the following conditions apply:

$$x < (r1 - r2) \text{ and } x < (r3 - r4) \quad [2]$$

The arrangement of the rod-shaped control element 42 between the cam disks 53 and 57 has the effect that all the combinations of angular positions of the first arm 5 and of the second arm 9 in the joints 3, 7 are locked if the axis of the rod-shaped control element 42 extends through the two locking segments 21, 31.

The cam disks 53, 57 can be detachably arranged on the joints 3, 7. As a result, it is easily possible to adapt the locking sector by replacing cam disks.

In FIG. 2, a rod-shaped control element 42 of fixed length 41 (L) is represented, which is pressed against the cam disk 53, for example, by a tension spring or a compression spring, not shown, which is arranged on the first arm 5.

In the context of the embodiments described herein, the rod-shaped control element 42 can be configured as a telescopic rod with a compression spring, wherein the length L1 of the telescopic rod, in the telescoped state, corresponds to the length L of formula [1], and the length L2 of the telescopic rod in the extended state satisfies the condition:

$$L2 > A - (r2 + r4) \quad [3]$$

A spring-loaded telescopic rod having these dimensions will bear with its ends against the two curves of the cam disks 53, 57, without any rattle, over the entire adjustment area of the monitor bracket 15.

The mode of action of the coupling mechanism is described in further detail with reference to FIG. 2. In the example of FIG. 2, the first arm 5 is slightly inclined relative to the installation surface 14 in the direction of the flat panel display, which is not shown. The second arm 9 is pivoted only slightly away from the first arm 5. If one leaves the pivoting of the first arm in the shoulder joint 3 unchanged, then the elbow joint 7 can be pivoted without inhibition over the entire permissible pivot range between the stops 58 and 59. This is true when the rod-shaped control element 42 is located in the sector 22 (S2) of the cam disk 53 between the stop 55 and the transition area 25.

If one starts again with the position of the joints 3, 7 shown in FIG. 2, and if one pivots the first arm 5 in the shoulder joint 3 counterclockwise without pivoting the elbow joint 7, the further movement of the first arm 5 is inhibited and blocked as a result of the lower end of the rod-shaped control element 42 running against the transition area 25 of the cam disk 53, in which the radius of the curve increases continuously.

The locking of the pivoting movement of the first arm 5 can be undone by pivoting the second pivot arm 9 in the shoulder joint 7 clockwise until the upper end of the rod-shaped control element 42 has reached the transition area 35, and, during further clockwise pivoting, the sector 32 (E2). Further pivoting in the shoulder joint 7 is possible until the stop 59 has been reached.

If the upper end of the rod-shaped control element 42 is in the sector 32 (E2) of the elbow joint 7, the first arm 5 can be moved in the entire range of the sectors 21 (S1) and 22 (S2) between the stops 54 and 55 without inhibition. The angles of the sectors 22 (S1) and 31 (E1) determine the size of the locked area. The angles of the sectors are determined by the kinematics of the monitor bracket and the position of the collision-endangered areas with the operating element 2. The locked area is decreased by decreasing the angles of the locking sectors 21 (S1) and 31 (E1).

The device can be configured to lock all the joint positions of the joints 3, 7 and of the first arm 5 and of the second arm 9 if the axis of the rod-shaped control element 42 extends through the two locking sectors 21 (S1) and 31 (E1).

In some embodiments, it is provided that control element 42 that comprises locking means is arranged on the first arm (5), wherein a first locking means acts on the shoulder joint 3 and a second locking means acts on the elbow joint 7, and in that, with the first locking means, the movement of the shoulder joint 3 about the first horizontal axis 4 can be blocked in a rotation direction, and in that, with the second locking means, the movement of the elbow joint 7 about the second horizontal pivot axis 8 can be blocked in one rotation direction, and in that the locking means are controlled by means of a control, which locks the movement of a joint 3, 7 in one rotation direction, if a predetermined collision-endangered locking area is reached by continuing the movement of the flat panel display 12, wherein the collision-endangered locking area is determined by a combination of angular positions of the first arm 5 with the shoulder joint 3 and with the elbow joint 7. The determination of the angular positions in the joints 3, 7 can occur by way of rotary encoders whose measurement values are supplied to an electronic control, wherein an electromagnetic locking device can be activated and deactivated.

Moreover, it is provided that the two joints 3, 7 can be locked by the control element 42. In particular, it is advantageous if, in a parked position of the flat panel display 12, the first horizontal pivot axis 4 and the second horizontal pivot axis 8 as well as the vertical rotation axis 13 are locked. When the mobile diagnostic device 1 is moving, this effectively prevents the flat panel display 12 from performing uncontrolled movements that would lead to a collision of the flat panel display 12 with other apparatuses or with parts of a building.

In some embodiments, the first horizontal pivot axis 4 and the vertical rotation axis 13 of the shoulder joint 3 can be locked simultaneously with a single manually actuated mechanical brake.

Furthermore, in some embodiments, the shoulder joint 3 and the elbow joint 7 can be equipped with servomotors that provide motor assistance to a manually performed movement of the flat panel display 12, wherein a servo control prevents the movement of the monitor bracket 15 into the collision-endangered locking area by inhibition of the servo assistance of the servomotors. The collision-endangered area is determined in a table of the control program of the servo control.

Figure 3A:
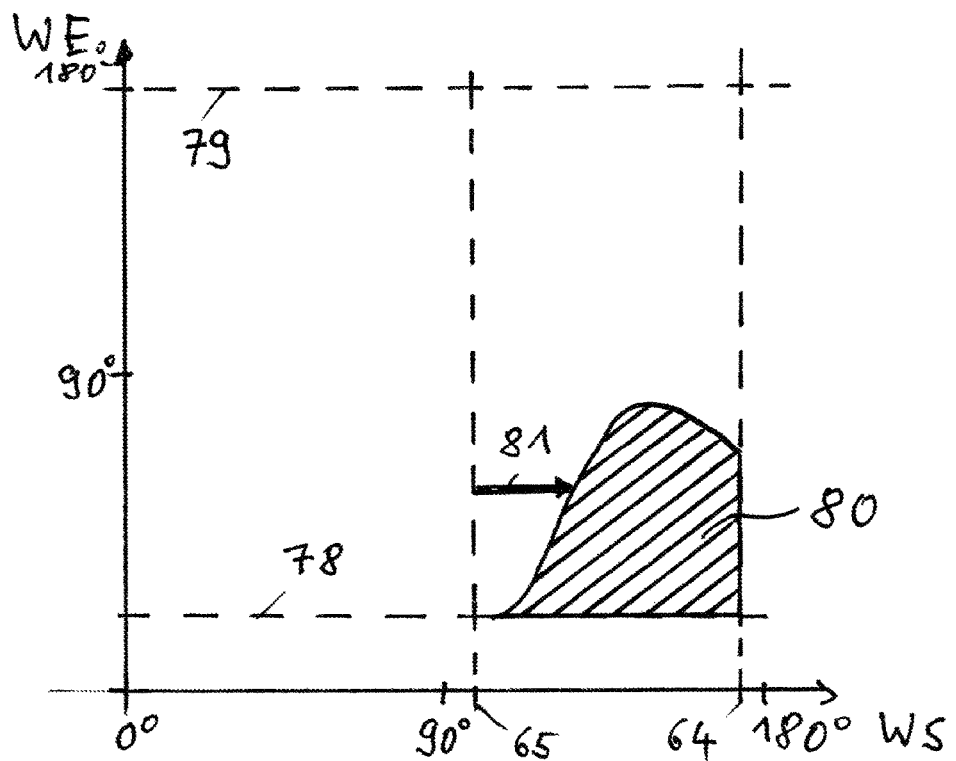
FIG. 3a: Pivot angles in the shoulder joint and in, the elbow joint.
Figure 3B:
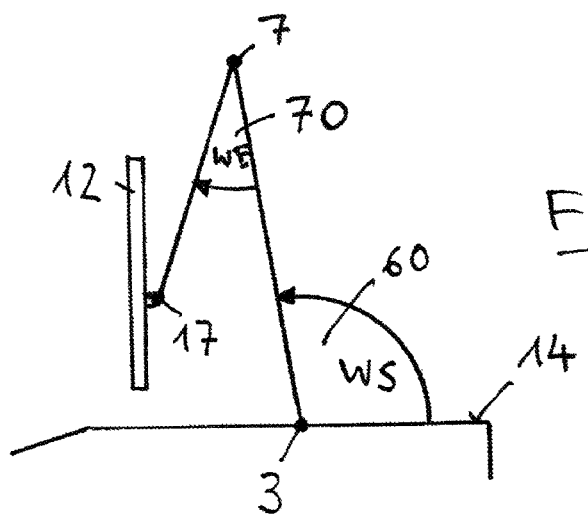
FIG. 3b: Pivot angles and collision-endangered area.

In FIG. 3b, the adjustment area of the monitor arm is represented in a diagram showing the collision-endangered area 80. The pivot angles 60 (WS) in the shoulder joint 3 and pivot angles 70 (WE) in the elbow joint 7 are represented diagrammatically in FIG. 3a. The limit angles of the pivoting movement in the shoulder joint 3 are represented by the broken lines 65 (associated with the stop 55) and 64 (associated with the stop 54). The limit angles of the pivoting movement in the elbow joint 7 are represented by the dashed lines 78 (associated with the stop 58) and 79 (associated with, the stop 59). Within the area formed by the dashed lines 78, 79, 64, 65, the collision-endangered area 80 as well as a path 81 are drawn. If one moves the monitor arm along the path 81, starting at the stop 55, e.g., on the dashed line 65, in such a manner that the pivot angle 70 (WE) in the elbow joint 7 remains unchanged, then the path at the tip of the arrow reaches the collision-endangered area 80. The pivot angle combinations in the crosshatched area 80 are blocked for the movement of the monitor arm by way of the devices and components described herein. At the end of the path 81 represented in the drawing, an additional enlargement of the pivot angle 60 (WS) is no longer possible without increasing the pivot angle 70 (WE). At the end of the path 81, a reduction of the pivot angle 70 by the control means is also blocked.

The path 81 can be continued in such a manner that the collision-endangered area is circumvented.

The embodiments described herein relate to a manually adjustable monitor bracket 15 for a flat panel display 12 of a mobile diagnostic device 1 with a shoulder joint 3 rotatably mounted on an installation surface 14 about a vertical rotation axis 13, at which shoulder joint 3 a first arm 5 is mounted such that it can be pivoted about a first horizontal pivot axis 4 by a pivot angle 60 (WS) between a pivot angle 64, which is associated with a stop 54, and a pivot angle 65, which is associated with a stop 55, wherein, on the side of the first arm 5, which faces away from the shoulder joint 3, an elbow joint 7 with a second horizontal pivot axis 8 parallel to the first horizontal pivot axis 4 and with a second arm 9 is arranged, wherein, between the first arm 5 and the second arm 9, a pivot axis 70 (WE) of the elbow joint 7 can be adjusted between a pivot angle 78, which is associated with a stop 58, and a pivot axis 79, which is associated with a stop 59, and wherein the second arm 9 comprises a hand joint 17, which supports an adjustable flat panel display 12, and wherein the monitor bracket 15 comprises a device for preventing a collision of the flat panel display 12 with the surface of the mobile diagnostic device 1, wherein a collision-endangered area 80 is determined by a number of value pairs of pivot angles 60 (WS) of the shoulder joint 3 and pivot angles 70 (WE) of the elbow joint 7, wherein the device for preventing a collision limits the movement of the monitor bracket 15 in such a manner that a movement in a direction about the first horizontal pivot axis 4 or in a direction about the second horizontal pivot axis 8 is blocked if continuing the movement about the pivot axes 4, 8 would lead to the value pairs including the pivot angles 60 (WS) of the shoulder joint 3 and of the pivot angles 70 (WE) of the shoulder joint 7 that are contained in the number of value pairs of the collision-endangered area 80.

In some of the embodiments described herein, it is provided that the device for preventing a collision comprises an electronic control, which controls the electromechanically controllable free running states on the axes 4, 8 in such a manner that the value pairs consisting of the pivot angles 60 (WS) of the shoulder joint 3 and the pivot angles 70 (WE) of the elbow joint 7 in the number of the value pairs of the collision-endangered area 80 are blocked, wherein the angular positions of the joints 3, 7 in the axes 4, 8 are determined by the rotary encoder and supplied to the electrical control, wherein the number of the value pairs of the collision-endangered area 80 are stored in a look-up table of a memory of the electronic control.

In some of the embodiments described herein, it is provided that the monitor bracket 15 comprises servomotors in the axes 4, 8 for motor assistance of the manual movement, and that the servomotors are controlled by an electronic control in such a manner that the value pairs consisting of the pivot angles 60 (WS) of the shoulder joint 3 and the pivot angles 70 (WE) of the elbow joint 7 in the number of the value pairs of the collision-endangered area 80 are blocked, wherein the angular positions of the joints 3, 7 in the axes 4, 8 are determined by rotation sensors and supplied to the electronic control, wherein the number of the value pairs of the collision-endangered area 80 are stored in a lookup table of a memory of the electronic control.

In some of the embodiments described herein, it is provided that the device for preventing a collision comprises a cam disk 53 in the shoulder joint 3 with stops 54, 55, a cam disk 57 in the elbow joint with stops 58, 59, and a rod-shaped control element 42, which is slidably arranged on the first arm 5 and one end of which is in operative connection with the cam disk 53 of the shoulder joint 3 while the other end is in operative connection with the cam, disk 57 of the elbow joint 7, wherein the cam disk 53 of the shoulder joint 3 comprises a locking segment 21 and a release segment 22, and the cam disk 57 of the elbow joint 7 comprises a locking segment 31 and a release segment 32, wherein the locking segments 21, 31 reproduce the value pairs of the pivot angles 60 (WS) and pivot angles 70 (WE) from the number of the value pairs of the collision-endangered area 80, wherein the curves of the cam disks 53, 57 are composed of segments of a circular arc whose center is the horizontal pivot axis 4, 8 of the respective joint 3, 7, wherein the segments of a circular arc of the respective cam disks 53, 57 are consistently connected to one another in a respective transition area 25, 35, wherein the locking segments 21, 31 comprise segments of a circular arc with a larger radius 23, 33 than the radius 24, 34 of the segments of a circular arc of the adjacent release segments 22, 32, and the rod-shaped control element 42 is arranged in the plane of the cam disks 53, 57 and in each case perpendicular to the horizontal pivot axes 4, 8, and has a length L 41 minus a mechanical clearance, said length corresponding to the distance A 40 between the pivot axes 4, 8, minus the sum of the radius 24 of the segment of a circular arc of the release segment 22 and the radius 33 of the segment of a circular arc of the locking segment 31.

In some of the embodiments described herein, it is provided that the rod-shaped control element 42 at each of its ends includes a roller that rolls on the associated cam disk 53, 57. It is also provided that the rod-shaped control element 42 is formed as a telescopic rod with a minimum length of length L 41.

It is advantageous if the cam disks for determining the collision-endangered area 80 can be exchanged, and the locking segments 21, 31 and the release segments 22, 32 can be selected from a modular system.

LIST OF REFERENCE NUMBERS

1 Mobile diagnostic device
2 Operating element
3 Shoulder joint
4 First horizontal pivot axis
5 First arm
6 Pivot direction
7 Elbow joint
8 Second horizontal pivot axis
9 Second arm
10 Pivot direction of the second arm 11 Hand
12 Flat panel screen
13 Vertical rotation axis
14 Installation surface
15 Monitor bracket
17 Hand joint
18 Third horizontal pivot axis
19 Support plate
20 Hand rotation axis
21 Pivot bearing
21 Locking sector
22 Fourth horizontal pivot axis
22 Release sector
23 Radius of the locking sector 21
24 Radius of the release sector 22
25 Transition area
31 Locking sector
32 Release sector
33 Radius of the locking sector 31
34 Radius of the release sector 32
35 Transition area
40 Distance between the axes 4 and 8
41 Length of the control element
42 Control element
53 Cam disk of the joint 3
54 Stop
55 Stop
57 Cam disk of the joint 7
58 Stop
59 Stop
60 Pivot angles WS of the shoulder joint
64 Pivot angles at the stop 54
65 Pivot angles at the stop 55
70 Pivot angles WE of the elbow joint
78 Pivot angles at the stop 58
79 Pivot angles at the stop 59
80 Area at risk for collisions
81 Path

What is claimed is:

1. A manually adjustable monitor bracket for a flat panel display of a mobile diagnostic device, the manually adjustable monitor bracket comprising:
   a shoulder joint configured to be mounted rotatably about a vertical rotation axis on a surface of the mobile diagnostic device, the shoulder joint defining a first horizontal pivot axis;
   a first arm having a first side and a second side opposite the first side, the first arm coupled to the shoulder joint at a first end of the first arm to form a first pivot angle between the first side of the first arm and the surface of the mobile diagnostic device;
   an elbow joint coupled to a second end of the first arm opposite the first end of the first arm, the elbow joint defining a second horizontal pivot axis parallel to the first horizontal pivot axis;
   a second arm coupled to the elbow joint at a first end of the second arm to form a second pivot angle between the second arm and the second side of the first arm, wherein a second end of the second arm opposite the first end of the second arm is configured to be coupled to the flat panel display; and
   a collision prevention device for preventing a collision of the flat panel display with the mobile diagnostic device based on a predetermined collision-endangered area, the collision prevention device comprising a shoulder cam disk disposed at the shoulder joint, an elbow cam disk disposed at the elbow joint, and a rod-shaped control element disposed on a perimeter of the shoulder cam disk and a perimeter of the elbow cam disk,
   wherein the perimeter of the shoulder cam disk includes a plurality of stops defining a range of first pivot angle values for the first pivot angle, wherein the first arm is configured to be pivoted about the first horizontal axis to vary a value of the first pivot angle within the range of the first pivot angle values,
   wherein the perimeter of the elbow cam disk includes a plurality of stops defining a range of second pivot angle values for the second pivot angle, wherein the second arm is configured to be pivoted about the second horizontal axis to vary a value of the second pivot angle within the range of the second pivot angle values,
   wherein the predetermined collision-endangered area comprises a predetermined plurality of value pairs, each value pair of the plurality of value pairs comprising a first pivot angle value and a second pivot angle value,
   wherein the collision prevention device is configured to block a movement of the first arm about the first horizontal pivot axis or a movement of the second arm about the second horizontal pivot axis if the movement of the first arm or the movement of the second arm would cause the values of the first pivot angle and the second pivot angle to correspond to a value pair contained in the predetermined plurality of value pairs of the predetermined collision-endangered area.

2. The manually adjustable monitor bracket of claim 1, wherein the perimeter of the shoulder cam disk further comprises a shoulder locking circular arc segment having a radius relative to the first horizontal pivot axis and a shoulder release circular arc segment having a radius relative to the first horizontal pivot axis,
   wherein the perimeter of the elbow cam disk further comprises an elbow locking circular arc segment having a radius relative to the second horizontal pivot axis and an elbow release circular arc segment having a radius relative to the second horizontal pivot axis,
   wherein the radius of the shoulder release circular arc segment is smaller than the radius of the shoulder locking circular arc segment,
   wherein the radius of the shoulder locking circular arc segment is equal to the radius of the elbow locking circular arc segment,
   wherein the radius of the shoulder release circular arc segment is equal to the radius of the elbow release circular arc segment,
   wherein the rod-shaped control element is disposed along the first arm, a first end of the rod-shaped control element is in an operative connection with the shoulder cam disk, and a second end of the rod-shaped control element is in an operative connection with the elbow cam disk,
   wherein the rod-shaped control element is disposed perpendicular to the first and second horizontal pivot axes and has a length L approximately equal to a distance A between the first horizontal pivot axis and the second horizontal pivot axis, minus the sum of the radius of the shoulder locking circular arc segment and the radius of the shoulder release circular arc segment, such that the rod-shaped control element prevents the shoulder locking segment and the elbow locking segment from being simultaneously aligned with the first arm.

3. The manually adjustable monitor bracket of claim 2, wherein the first end of the rod-shaped control element is configured to travel along the perimeter of the shoulder cam disk and wherein the second end of the rod-shaped control element is configured to travel along the perimeter of the elbow cam disk.

4. The manually adjustable monitor bracket of claim 2, wherein the rod-shaped control element has an adjustable length, wherein a minimum length of the rod-shaped control element is the length L.

5. The manually adjustable monitor bracket of claim 2, wherein the shoulder cam disk and the elbow cam disk are exchangeable.

* * * * *